(12) United States Patent
Heatherington et al.

(10) Patent No.: US 9,149,595 B2
(45) Date of Patent: Oct. 6, 2015

(54) RESPIRATORY MASK ASSEMBLY

(71) Applicant: Stuart Heatherington, Chapel Hill, NC (US)

(72) Inventors: Stuart Heatherington, Chapel Hill, NC (US); Stanley S. Coe, Raleigh, NC (US)

(73) Assignee: Stuart Heatherington, Chapel Hill, NC (US)

( * ) Notice: Subject to any disclaimer, the term of this patent is extended or adjusted under 35 U.S.C. 154(b) by 456 days.

(21) Appl. No.: 13/672,946

(22) Filed: Nov. 9, 2012

(65) Prior Publication Data

US 2013/0131534 A1    May 23, 2013

Related U.S. Application Data

(60) Provisional application No. 61/562,056, filed on Nov. 21, 2011.

(51) Int. Cl.

| | | |
|---|---|---|
| *A62B 18/08* | (2006.01) | |
| *A61M 16/00* | (2006.01) | |
| *A61M 16/06* | (2006.01) | |
| *A61B 5/08* | (2006.01) | |
| *A61B 5/097* | (2006.01) | |
| *A61M 16/04* | (2006.01) | |
| *A61M 16/08* | (2006.01) | |

(52) U.S. Cl.
CPC ............ *A61M 16/0666* (2013.01); *A61B 5/082* (2013.01); *A61B 5/097* (2013.01); *A61M 16/0057* (2013.01); *A61M 16/0493* (2014.02); *A61M 16/0816* (2013.01)

(58) Field of Classification Search
None
See application file for complete search history.

(56) References Cited

U.S. PATENT DOCUMENTS

| | | | | | |
|---|---|---|---|---|---|
| 2,677,371 | A | * | 5/1954 | Loredo Serra | 128/205.12 |
| 4,782,832 | A | * | 11/1988 | Trimble et al. | 128/207.18 |
| 5,676,133 | A | * | 10/1997 | Hickle et al. | 128/205.12 |
| 7,506,649 | B2 | | 3/2009 | Doshi et al. | |
| 8,061,357 | B2 | * | 11/2011 | Pierce et al. | 128/207.18 |
| 8,215,308 | B2 | * | 7/2012 | Doshi et al. | 128/207.18 |
| 8,291,906 | B2 | | 10/2012 | Kooij et al. | |
| 2004/0216747 | A1 | * | 11/2004 | Jones et al. | 128/206.21 |
| 2006/0042631 | A1 | * | 3/2006 | Martin et al. | 128/207.18 |
| 2006/0283461 | A1 | * | 12/2006 | Lubke et al. | 128/207.11 |
| 2008/0223375 | A1 | * | 9/2008 | Cortez et al. | 128/207.18 |
| 2009/0032026 | A1 | * | 2/2009 | Price et al. | 128/207.11 |
| 2009/0101147 | A1 | * | 4/2009 | Landis et al. | 128/204.18 |
| 2009/0241961 | A1 | * | 10/2009 | McAuley et al. | 128/205.25 |
| 2010/0229872 | A1 | * | 9/2010 | Ho | 128/206.25 |
| 2010/0282263 | A1 | * | 11/2010 | Asada et al. | 128/206.15 |
| 2011/0067704 | A1 | * | 3/2011 | Kooij et al. | 128/207.18 |

* cited by examiner

*Primary Examiner* — Jason Flick
*Assistant Examiner* — Eric Bryant
(74) *Attorney, Agent, or Firm* — NK Patent Law

(57) ABSTRACT

A respiratory mask assembly is provided. The assembly includes at least one post having a nasal engaging portion on about a first end thereof for delivering treatment gases to the nasal cavity of a patient. A mask having an inlet for receiving treatment gases from a fluid source and at least one receptacle for being sealably engaged with a respective one of the at least one post for delivering treatment gases from the inlet through the receptacle and into the nasal cavity of the patient is provided. The mask is configured for selective sealable engagement with the patient's mouth, patient's nose, or both the patient's mouth and the patient's nose.

6 Claims, 3 Drawing Sheets

RESPIRATORY MASK ASSEMBLY

CROSS-REFERENCE TO RELATED APPLICATIONS

This application claims priority to U.S. Provisional Patent Application No. 61/562,056 filed on Nov. 21, 2011, the contents of which are hereby incorporated by reference in their entirety.

TECHNICAL FIELD

This disclosure is related to a respiratory mask assembly, and more particularly a respiratory mask assembly having a nostril engaging portion for providing sealable engagement with a treatment fluid.

BACKGROUND

Continuous positive air pressure (CPAP) masks are used for treating patients having any number of sleeping or breathing disorders during sleeping. The CPAP mask delivers a treatment fluid, such as ambient air or oxygen enriched air to a patient under a predetermined or desired pressure setting.

CPAP masks suffer from many disadvantages. For example, CPAP masks are bulky, making them less aesthetically and ergonomically pleasing. CPAP masks must provide sealable engagement with the patient's skin in order to maintain a sealed environment for achieving the desired pressure for treatment fluid delivery. This sealable engagement leaves wear marks on the patient's skin and may require undesirable amounts of time for the wear marks to disappear. Accordingly, many patients feel uncomfortable in public until the wear marks have disappeared, and male patients may not be able to shave their faces and female patients not be able to apply makeup until the wear marks have disappeared.

Due to the bulky nature of conventional CPAP masks, the masks occupy a large portion of a person's face. This restricts the person's ability to move their head during sleep because laying on the side of one's face may contact the CPAP mask and dislodge the mask from sealable engagement with the patient, thereby evacuating the pressure in the mask assembly. This is undesirable as either the patient is not receiving treatment gases under the ideal pressures or the patient is awakened.

Accordingly, there is a need for an improved CPAP mask that addresses the disadvantages associated with conventional CPAP machines.

SUMMARY

This Summary is provided to introduce a selection of concepts in a simplified form that are further described below in the Detailed Description of Illustrative Embodiments. This Summary is not intended to identify key features or essential features of the claimed subject matter, nor is it intended to be used to limit the scope of the claimed subject matter.

Disclosed herein is a respiratory mask assembly. The mask assembly includes a nasal engaging device having at least one post with a nasal engaging portion on about a first end thereof for delivering treatment gases to the nasal cavity of a patient. A mask is provided and has an inlet for receiving treatment gases from a fluid source and at least one receptacle for being sealably engaged with a respective one of the at least one post for delivering treatment gases from the inlet through the receptacle and into the nasal cavity of the patient.

According to one or more embodiments, the nasal engaging portion includes a flange portion configured for engaging with a sheet having an adhesive applied thereon for being adhered and providing sealable engagement with the nostrils of the patient.

According to one or more embodiments, the at least one post includes a circumferentially extending portion on a second end thereof that is configured for selective engagement with the at least one receptacle.

According to one or more embodiments, the at least one post includes a connector on a second end thereof for connecting with the at least one receptacle.

According to one or more embodiments, the inlet includes a swivel joint for allowing swiveling movement of the inlet about the mask.

According to one or more embodiments, the mask assembly is configured for use with a continuous positive airway pressure (CPAP) machine.

According to one or more embodiments, the mask assembly includes a hose for providing flowthrough of treatment gases from the fluid source to the inlet.

According to one or more embodiments, a CPAP mask is provided. The mask includes an inlet for receiving treatment gases from a fluid source, and at least one receptacle for being engaged with a post in sealable engagement with the nasal cavity of a patient and for delivering treatment gases from the inlet through the receptacle and into the nasal cavity of the patient.

According to one or more embodiments, the mask includes a pair of spaced-apart receptacles, each for engaging a respective post in sealable engagement with each nostril of the patient.

According to one or more embodiments, the nasal engaging device includes a seal in selective engagement with the adhesive.

According to one or more embodiments, a respiratory mask assembly is provided. The mask assembly includes a nasal engaging device having a nasal engaging portion and configured for delivering treatment gases to the nasal cavity of a patient. A mask is provided and has an inlet for receiving treatment gases from a fluid source and configured for providing sealable engagement with the nasal engaging device and delivering treatment gases from the inlet through the receptacle and into the nasal cavity of the patient.

According to one or more embodiments, a CPAP mask assembly is provided. The mask assembly includes a nare engaging assembly having a pair of posts, each post having a flange that defines an opening therein for allowing flowthrough of treatment gas into the patient's nasal cavity, and a pressure sensitive adhesive applied to each flange and configured for sealably engaging with the patient's nare. The mask assembly may further include a mask including a body having a pair of receptacles, a socket recess, and a chamber for allowing flowthrough of treatment gases to the patient's mouth area. The mask assembly may further include an inlet including a ball joint defining a plurality of vent openings for allowing flowthrough of treatment gases and configured for being received within the socket recess defined within the mask to allow pivotable movement of the inlet about the mask. The mask assembly may further include a pair of tubes, each tube extending from each outlet port to each post for delivery treatment gases to the nare engaging assembly. The CPAP mask assembly has a first operation of use in which a pad having a pressure sensitive adhesive on opposing sides adheres the mask assembly to the patient's face such that treatment gases are delivered to the patient's mouth and nasal area, and a second operation of use in which the mask assembly further comprises a panel that covers the chamber for preventing flowthrough of treatment gases to the patient's mouth area such that treatment gases are delivered only to the patient's nasal area, and a third operation of use in which the mask includes a plurality of plugs that seal the outlet ports such that treatment gages are delivered only to the patient's mouth area.

BRIEF DESCRIPTION OF THE DRAWINGS

The foregoing summary, as well as the following detailed description of preferred embodiments, is better understood when read in conjunction with the appended drawings. For the purposes of illustration, there is shown in the drawings exemplary embodiments; however, the presently disclosed invention is not limited to the specific methods and instrumentalities disclosed. In the drawings.

DETAILED DESCRIPTION

The presently disclosed invention is described with specificity to meet statutory requirements. However, the description itself is not intended to limit the scope of this patent. Rather, the inventors have contemplated that the claimed invention might also be embodied in other ways, to include different steps or elements similar to the ones described in this document, in conjunction with other present or future technologies.

Figure 1:
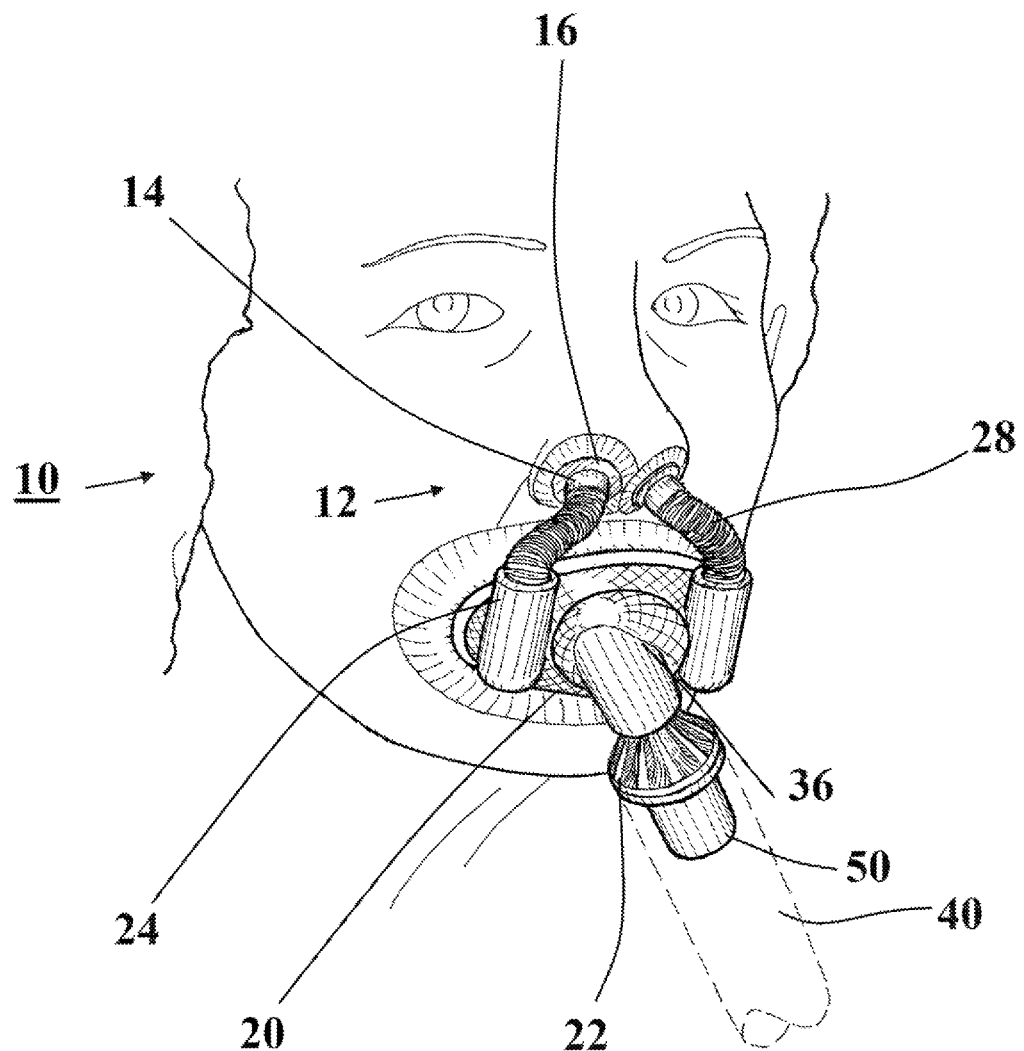
FIG. 1 illustrates a perspective view of a respiratory mask and a patient for being treated according to one or more embodiments disclosed herein.

FIG. 1 illustrates a respiratory mask assembly installed upon a patient 1. The mask assembly is generally designated as 10 throughout the drawings. The mask assembly 10 includes a nasal or nare engaging device 12 having at least one post 14 with a nasal engaging portion 16 on about a first end thereof for delivering treatment gases to the nasal cavity of the patient 1. The post 14 may be configured for providing a flush, sealable engagement with the patient's nares.

The mask assembly 10 may include a mask 20 having an inlet 22 for receiving treatment gases from a fluid source and at least one receptacle or outlet port 24 for being sealably engaged with the post 14. The post 14 may be selectively engageable with the receptacle 24, such that the engagement is permanent or only when desired by the patient. Alternatively, the post 14 may be engageable directly with a tube 28 carrying treatment gases therethrough.

Figure 2:
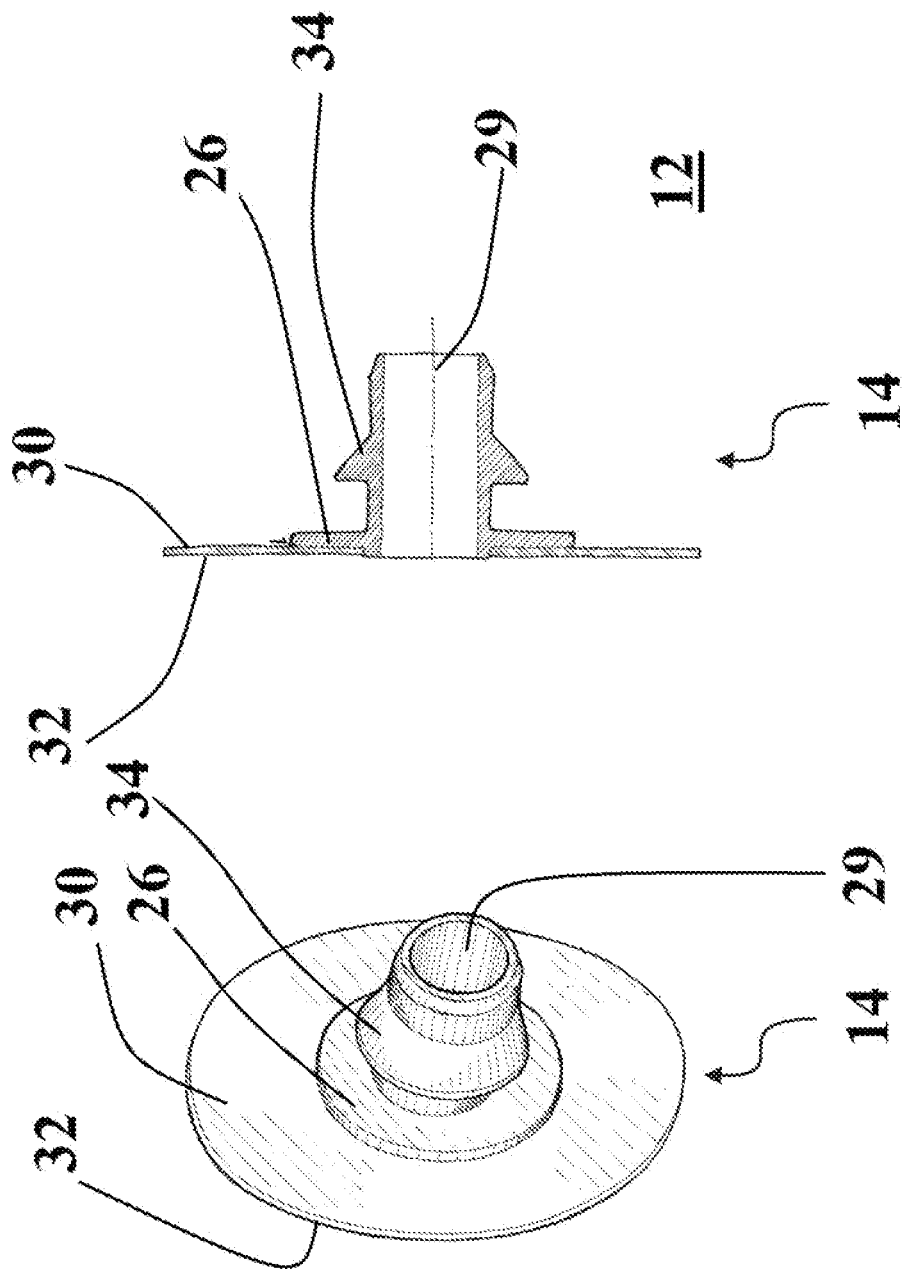
FIGS. 2A and 2B illustrate respective perspective and side views of a nasal engaging device for use with a respiratory mask according to one or more embodiments disclosed herein.

FIGS. 2A and 2B illustrate the nasal engaging device 12 in greater detail. The post 14 includes a flange portion 26 configured for engaging with a sheet 30 having an adhesive 32 applied thereon, or alternatively, a layer of adhesive 32, for being adhered and providing sealable engagement with the nostrils of the patient. The sheet 30 may have any desired shape, and may preferably include an opening therein for allowing flowthrough in an opening 29 defined in the post 14. The adhesive 32 may be a pressure sensitive adhesive such that the sheet 30 may be adhered and removed from the patient's nostrils as desired. The post 16 includes a circumferentially extending portion 34 on a second end thereof that is configured for selective engagement with the at least one receptacle 24.

Figure 3:
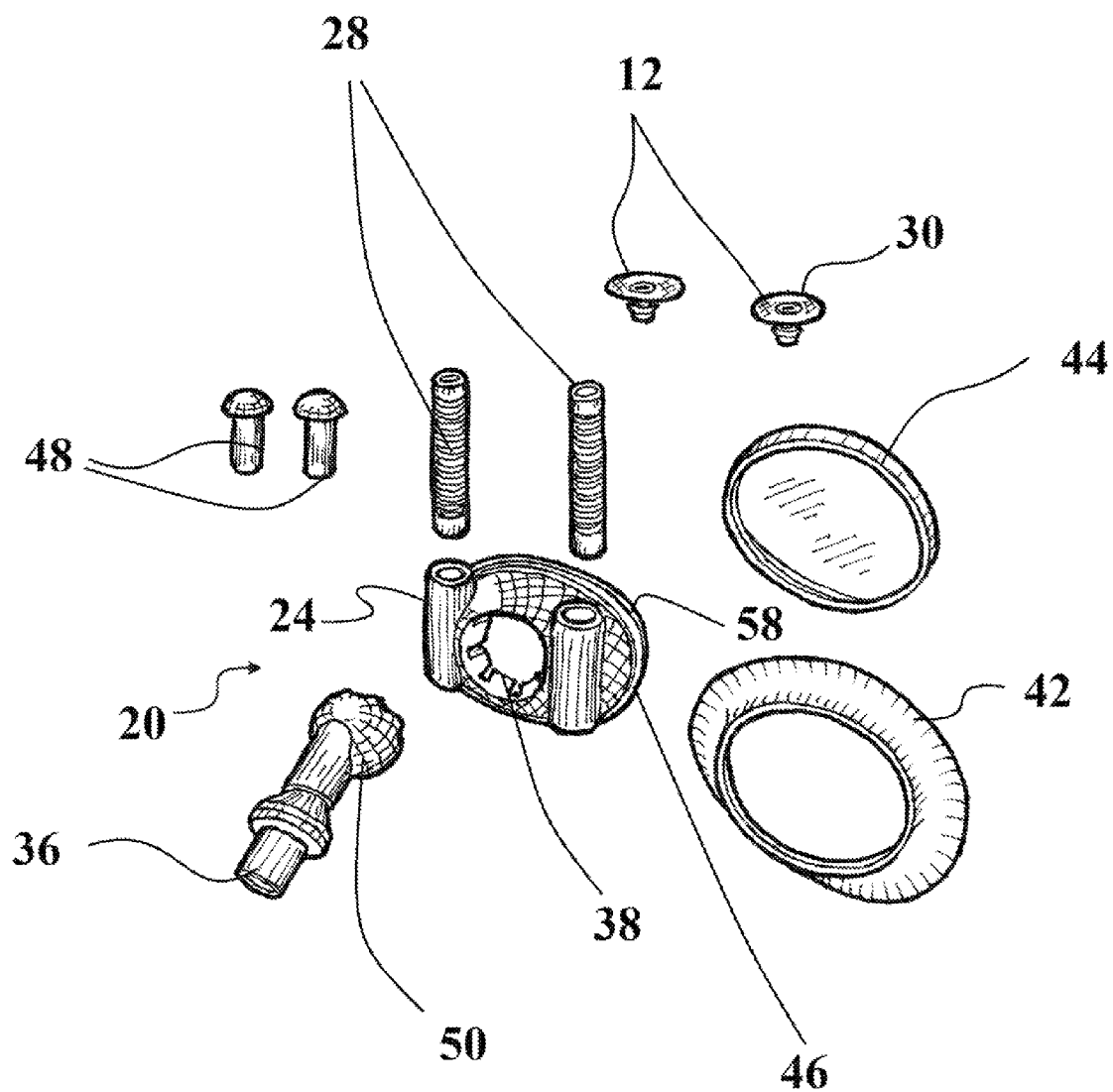
FIG. 3 illustrates a perspective view of a mask according to one or more embodiments disclosed herein.

As illustrated in FIG. 3, the inlet 22 may include a swivel joint 36 for allowing swiveling movement of the inlet 22 about the mask assembly 20. The inlet 22 may be a hose 40 for providing flowthrough of treatment gases from the fluid source to the inlet.

The receptacle 24 may include a tube 28 configured for flexible movement to position the post 12 to various sizes of respective patients' noses. As illustrated in more detail in FIG. 3, the mask 20 is configured for sealable engagement with the patient's mouth by an adhesive pad 42 selectively engageable therewith and carried by the mask body 46. Within the mask body 46 is defined a chamber 58 through which treatment gases flow from the inlet 22. In this manner, in one operative condition, the mask assembly 20 is sealably engaged with both the patient's mouth area while the nare engaging assembly 12 is also engaged with the patient's nares or nasal assembly. In this operative condition, treatment gases are being supplied to both the patient's mouth and their nasal area simultaneously. The mask body 46 may further define a socket recess 38 for cooperating with a joint described further herein.

Alternatively, panel 44 is provided for sealable engagement with the mask assembly 20 in order to seal off the chamber 58 so that treatment gases do not pass into the area surrounding the patient's mouth and instead pass only through to the nare engaging assembly 12. In this manner, the one or more devices 10 disclosed herein are appropriately configured for both CPAP applications in which the patient receives treatment gases to both their mouth and nose and in CPAP applications where the patient receives treatment gases to only their nose. Additionally, one or more plugs 48 may be provided for use with the mask 20 to seal receptacles 24 if the patient does not desire use of the nasal engaging configuration provided herein. Accordingly, the mask assembly 10 described herein has three distinct modes of operation: one in which treatment gases are being supplied to the patient's mouth only, one in which treatment gases are being supplied to the patient's nose only, and one in which treatment gases are being supplied to the patient's nose and mouth.

The patient may install a new adhesive pad 42 and sheet 30 after each use.

In one or more embodiments, the inlet may further include a ball and socket joint 50 as illustrated in FIG. 3, with ball being represented as 50 and socket recess being represented by 38. The ball and socket joint allows for rotational movement of the inlet 22. The ball 50 may define a plurality of vent slots 52 for allowing flow of treatment gases therethrough. The vent slots 52 may be adjustable in size and location such that manipulation of all exhaled fluids such as Carbon Dioxide from the patient is controlled and titratable such that the flow rate of fluids can be altered to a desired setting.

In one or more embodiments, the mask body 46 may include an adjustable mechanism that allows the tubing from the post 14 to be altered, moved or elevated to accommodate a patient's facial structure, primarily the distance between the nose and the oral housing port on or inside body 46, thereby allowing for ideal facial angles and facial length that might add to a patient's comfort.

In one or more embodiments, the mask assembly may be provided as a short-term use product, such that the entire system is disposed of and replaced after a predetermined use period. For example, the mask assembly may be configured for use as a three month use product, such that the patient receives a new mask assembly every three months. Additionally, post 14 may be a disposable product.

While the embodiments have been described in connection with the preferred embodiments of the various figures, it is to be understood that other similar embodiments may be used or modifications and additions may be made to the described embodiment for performing the same function without deviating therefrom. Therefore, the disclosed embodiments should not be limited to any single embodiment, but rather should be construed in breadth and scope in accordance with the appended claims.

What is claimed:

1. A CPAP mask assembly comprising:
a nare engaging assembly having:
   a pair of posts, each post having a flange that defines an opening therein for allowing flowthrough of treatment gas into a patient's nasal cavity; and
   a pressure sensitive adhesive applied to each flange and configured for sealably engaging with a patient's nare;
a mask including a body having a pair of receptacles, a socket recess, and a chamber for allowing flowthrough of treatment gases to a patient's mouth area;
an inlet including a ball joint defining a plurality of vent openings for allowing flowthrough of treatment gases and configured for being received within the socket recess defined within the mask to allow pivotable movement of the inlet about the mask;
a pair of tubes, each tube extending from respective outlet ports to each post for delivery of treatment gases to the nare engaging assembly,
wherein the CPAP mask assembly has a first operation of use in which a pad having a pressure sensitive adhesive on opposing sides adheres the mask assembly to a patient's face such that treatment gases are delivered to the patient's mouth and a nasal area, and a second operation of use in which the mask assembly further comprises a panel that covers the chamber for preventing flowthrough of treatment gases to the patient's mouth area such that treatment gases are delivered only to the patient's nasal area, and a third operation of use in which the mask includes a plurality of plugs that seal the outlet ports such that treatment gages are delivered only to the patient's mouth area.

2. The CPAP mask assembly of claim 1, wherein the each of the posts comprise a circumferentially extending portion on an end thereof that is configured for selective engagement with the each receptacle of the pair of receptacles.

3. The CPAP mask assembly of claim 1, wherein the mask includes the ball joint defining a plurality of vents for allowing flowthrough of treatment gases and configured for being received within the socket joint defined within the mask to allow pivotable movement of the inlet about the mask.

4. The CPAP mask assembly of claim 1, wherein the flange is free of a protrusion extending into the patient's nostril such that sealable engagement with the patient's nostrils are provided only by the flange and the pressure sensitive adhesive.

5. A CPAP mask assembly comprising:
a nare engaging assembly having:
   a pair of posts, each post having a flange that defines an opening therein for allowing flowthrough of treatment gas into a patient's nasal cavity; and
   an adhesive applied to each flange and configured for sealably engaging with a patient's nare;
a mask including a body having a pair of receptacles, a socket recess, and a chamber for allowing flowthrough of treatment gases to a patient's mouth area;
an inlet for allowing flowthrough of treatment gases and configured for being received within the socket recess defined within the mask to allow pivotable movement of the inlet about the mask;
a pair of tubes, each tube extending from respective outlet ports to each post for delivery of treatment gases to the nare engaging assembly,
wherein the CPAP mask assembly has a first operation of use in which a pad having a pressure sensitive adhesive on opposing sides adheres the mask assembly to a patient's face such that treatment gases are delivered to the patient's mouth and a nasal area, and a second operation of use in which the mask assembly further comprises a panel that covers the chamber for preventing flowthrough of treatment gases to the patient's mouth area such that treatment gases are delivered only to the patient's nasal area, and a third operation of use in which the mask includes a plurality of plugs that seal the outlet ports such that treatment gages are delivered only to the patient's mouth area.

6. A CPAP mask assembly comprising:
a nare engaging assembly having:
   a pair of posts, each post having a flange that defines an opening therein for allowing flowthrough of treatment gas into a patient's nasal cavity; and
   a pressure sensitive adhesive applied to each flange and configured for sealably engaging with a patient's nare;
a mask including a chamber for allowing flowthrough of treatment gases to a patient's mouth area;
an inlet for allowing flowthrough of treatment gases;
a pair of tubes, each tube extending from respective outlet ports to each post for delivery of treatment gases to the nare engaging assembly,
wherein the CPAP mask assembly has a first operation of use in which treatment gases are delivered to the patient's mouth and a nasal area, and a second operation of use in which the mask assembly further comprises a panel that covers the chamber for preventing flowthrough of treatment gases to the patient's mouth area such that treatment gases are delivered only to the patient's nasal area, and a third operation of use in which the mask includes a plurality of plugs that seal the outlet ports such that treatment gages are delivered only to the patient's mouth area.

* * * * *